(12) United States Patent
Murdeshwar et al.

(10) Patent No.: US 12,733,951 B2
(45) Date of Patent: Sep. 15, 2026

(54) SURGICAL DEVICE WITH DUAL CUTTING AND SERVICE FEATURES

(71) Applicant: GYRUS ACMI, INC., Westborough, MA (US)

(72) Inventors: Nikhil M. Murdeshwar, Maple Grove, MN (US); Jordan R Golomb, Maple Grove, MN (US); Kester Julian Batchelor, Mound, MN (US); Joey Magno, Dudley, MA (US)

(73) Assignee: Gyrus ACMI, Inc., Westborough, MA (US)

( * ) Notice: Subject to any disclaimer, the term of this patent is extended or adjusted under 35 U.S.C. 154(b) by 664 days.

(21) Appl. No.: 17/649,696

(22) Filed: Feb. 2, 2022

(65) Prior Publication Data

US 2022/0240966 A1 Aug. 4, 2022

Related U.S. Application Data

(60) Provisional application No. 63/262,854, filed on Oct. 21, 2021, provisional application No. 63/145,261, filed on Feb. 3, 2021.

(51) Int. Cl.

| | |
|---|---|
| ***A61B 17/28*** | (2006.01) |
| ***A61B 17/32*** | (2006.01) |
| ***A61B 18/20*** | (2006.01) |

(52) U.S. Cl.

CPC ............ *A61B 17/32* (2013.01); *A61B 17/282* (2013.01); *A61B 18/20* (2013.01); *A61B 2017/320012* (2013.01)

(58) Field of Classification Search

CPC .................... A61B 17/32; A61B 17/28; A61B 2017/2901–2906; A61B 2017/2908; (Continued)

(56) References Cited

U.S. PATENT DOCUMENTS 4,091,880 A * 5/1978 Troutner ............ A61B 17/1628 173/217
4,288,882 A * 9/1981 Takeuchi ............... A61B 1/122 15/97.1

(Continued)

FOREIGN PATENT DOCUMENTS

EP 2241280 A2 * 10/2010 ............. A61B 18/22
KR 102346315 B1 * 1/2022 ......... A61B 1/00096

*Primary Examiner* — Darwin P Erezo
*Assistant Examiner* — Mitchell Brian Hoag
(74) *Attorney, Agent, or Firm* — Schwegman Lundberg & Woessner, P.A.

(57) ABSTRACT

A surgical device may include a housing configured for handling by a user and comprising a plurality of operator interfacing features. The device may also include a patient interfacing tip arranged at, or spaced apart from, a distal end of the housing and controllable by the operator interfacing features. The patient interfacing tip may include a pair of jaws configured to grasp tissue, an electrode on each jaw configured to seal tissue, and an articulating blade configured to cut tissue in a grasp of the pair of jaws. The device may also include an optical element extending from the housing to the patient interfacing tip and configured to emit laser energy to cut tissue, wherein the pair of jaws, electrode, and articulating blade are adapted for coarse cutting of tissue and the optical element is configured for precise cutting of tissue.

6 Claims, 9 Drawing Sheets

(58) Field of Classification Search

CPC .......... A61B 17/2909; A61B 2017/292; A61B 2017/293; A61B 2017/294; A61B 2017/320069; A61B 18/20; A61B 2018/0097; A61B 17/02; A61B 2017/291; A61B 2017/2911; A61B 2017/2912–2919; A61B 2017/2922–2929; A61B 2017/2931–2939; A61B 17/295; A61B 2017/2941–2948; A61B 2017/320071; A61B 2017/320072–32007; A61B 2017/32008; A61B 2017/320082–320089; A61B 2017/32009; A61B 17/320092; A61B 17/3201; A61B 17/3203; A61B 2017/32032; A61B 2017/32035; A61B 17/32037; A61B 18/22; A61B 2018/2005; A61B 18/201; A61B 2018/1442; A61B 18/1445; A61B 18/1447; A61B 2018/145; A61B 2018/1452; A61B 2018/1455; A61B 2018/1457; A61B 2018/00976; A61B 17/282; A61B 2017/320012; A61B 2018/0196; A61B 2018/00404; A61B 2018/00434; A61B 2018/00559; A61B 2018/00601; A61B 2018/0063; A61B 2018/00928; A61B 2018/00934; A61B 2018/00994; A61B 2018/00982; A61B 2018/2211; A61B 90/70; A61B 2090/701; A61B 1/122; A61B 1/126

See application file for complete search history.

(56) References Cited

U.S. PATENT DOCUMENTS 4,361,926 A * 12/1982 Brush ................ A61B 18/1402 606/49
5,035,695 A * 7/1991 Weber, Jr. .......... A61B 18/1402 606/49
5,300,087 A * 4/1994 Knoepfler ............. A61B 17/29 604/35
5,308,358 A * 5/1994 Bond ..................... A61B 17/29 606/174
5,320,617 A * 6/1994 Leach .................... A61B 18/24 604/21
5,375,589 A * 12/1994 Bhatta .................... A61B 1/122 600/104
5,403,311 A * 4/1995 Abele ................ A61B 18/1492 606/49
5,456,681 A * 10/1995 Hajjar .................... A61B 18/24 606/15
5,578,031 A * 11/1996 Wilk ...................... A61B 17/29 606/49
6,193,709 B1 * 2/2001 Miyawaki ...... A61B 17/320092 606/49
6,575,940 B1 * 6/2003 Levinson ......... A61B 17/00491 604/191
7,115,139 B2 * 10/2006 McClurken ........ A61B 18/1445 607/104
9,700,333 B2 * 7/2017 Strobl .................. A61B 17/285
10,548,623 B2 * 2/2020 Alsac ............. A61B 17/320016
12,357,374 B2 * 7/2025 Brustad .............. A61B 18/1445
2003/0109837 A1 * 6/2003 Mcbride-Sakal ...... A61B 1/122 606/159
2008/0295281 A1 * 12/2008 Kumaran .................. B08B 1/12 15/398
2013/0253489 A1 * 9/2013 Nau, Jr. ................. A61B 18/22 606/17
2014/0135740 A1 * 5/2014 Okoniewski ........... A61B 90/70 604/540
2014/0135804 A1 * 5/2014 Weisenburgh, II ... F15D 1/0015 606/169
2015/0142031 A1 * 5/2015 Faller ..................... A61B 90/70 606/169
2016/0089198 A1 * 3/2016 Arya .................. A61B 18/1482 600/317
2016/0175050 A1 * 6/2016 Arshonsky ............. A61B 18/18 606/41
2016/0346034 A1 * 12/2016 Arya ...................... A61B 18/22
2017/0000554 A1 * 1/2017 Yates ................. A61B 18/1445
2017/0156747 A1 * 6/2017 Worrell .............. A61B 17/2816
2017/0354476 A1 * 12/2017 Vasan ..................... B08B 1/143
2018/0242910 A1 * 8/2018 Marcotte .............. A61B 5/4893
2018/0333184 A1 * 11/2018 Leuck ................ A61B 18/1206
2018/0344427 A1 * 12/2018 Rosenbaum ........... A61B 90/70
2019/0223707 A1 * 7/2019 Fujiwara ................... B08B 1/12
2021/0196353 A1 * 7/2021 Gee ................ A61B 17/320092
2021/0330354 A1 * 10/2021 Einarsson ............ A61B 90/361
2021/0338307 A1 * 11/2021 Baril ...................... A61B 90/70
2022/0079625 A1 * 3/2022 Einarsson ............ A61B 90/361
2022/0110673 A1 * 4/2022 Boronyak .......... A61B 18/1445
2023/0056943 A1 * 2/2023 Vyas .................. A61B 1/00087
2023/0094567 A1 * 3/2023 Murdeshwar ...... A61B 18/1445 600/564
2023/0280556 A1 * 9/2023 Zhong .................... A61B 90/70 372/6
2023/0346212 A1 * 11/2023 Dovgan ................. A61B 1/127
2024/0003820 A1 * 1/2024 Shelton, IV ........... A61B 90/70
2024/0165649 A1 * 5/2024 Mandula .............. C09D 183/04
2024/0269713 A1 * 8/2024 McManus ............. B08B 7/0071
2025/0025211 A1 * 1/2025 Einarsson .......... A61B 1/00096
2025/0185800 A1 * 6/2025 Krzyzanowski ....... A61B 90/70
2025/0204922 A1 * 6/2025 Farrelly ........... A61B 17/12177

* cited by examiner

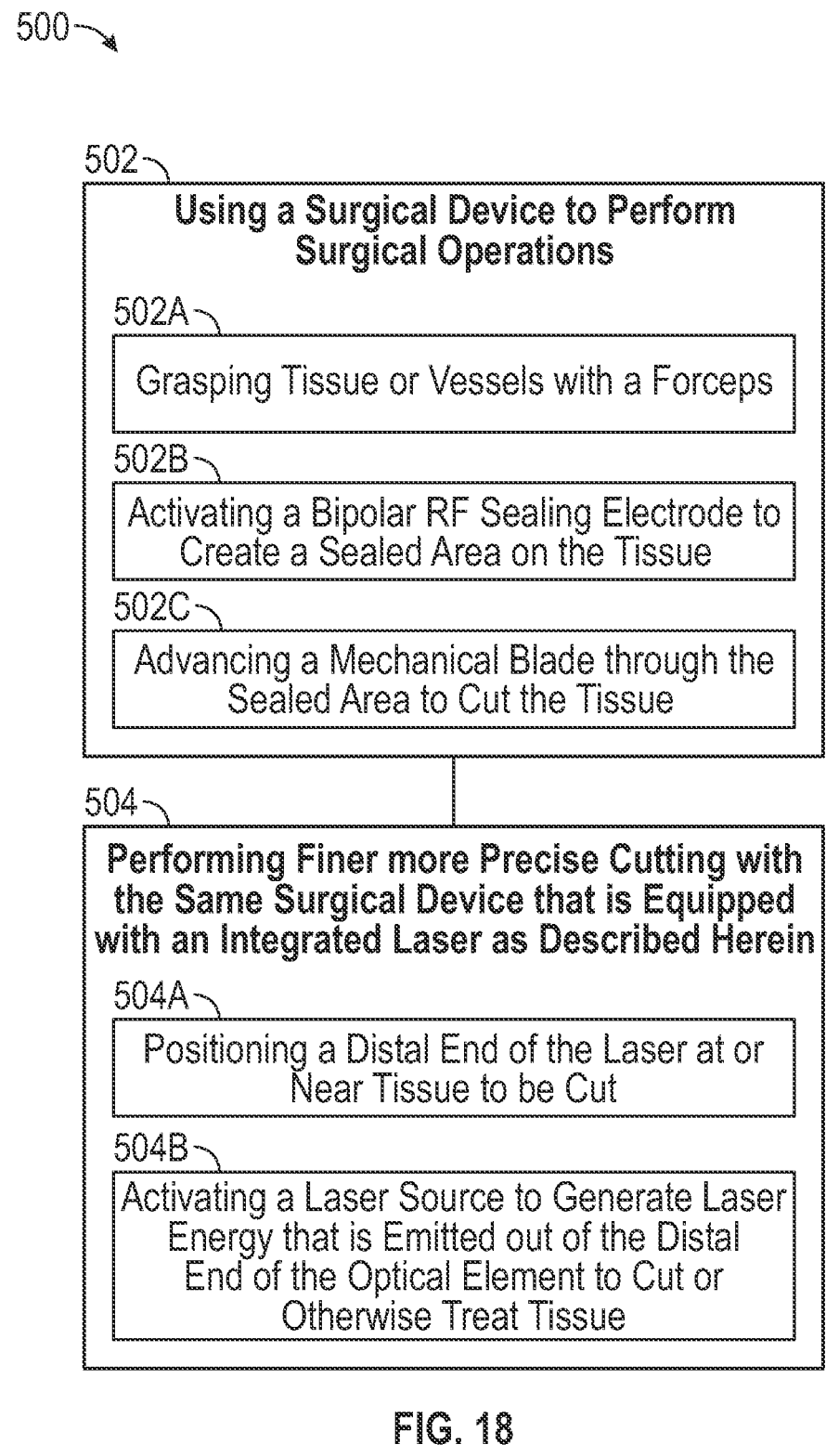

500

502
Using a Surgical Device to Perform Surgical Operations

502A
Grasping Tissue or Vessels with a Forceps

502B
Activating a Bipolar RF Sealing Electrode to Create a Sealed Area on the Tissue 502C
Advancing a Mechanical Blade through the Sealed Area to Cut the Tissue 504
Performing Finer more Precise Cutting with the Same Surgical Device that is Equipped with an Integrated Laser as Described Herein

504A
Positioning a Distal End of the Laser at or Near Tissue to be Cut

504B
Activating a Laser Source to Generate Laser Energy that is Emitted out of the Distal End of the Optical Element to Cut or Otherwise Treat Tissue

FIG. 18

SURGICAL DEVICE WITH DUAL CUTTING AND SERVICE FEATURES

CROSS-REFERENCE TO RELATED APPLICATIONS

The present application claims priority to U.S. Provisional Patent Application No. 63/145,261 entitled Surgical Device with Precision Functionality and filed on Feb. 3, 2021. The present application also claims priority to U.S. Provisional Patent Application No. 63/262,854 entitled Wiper on Laser Fiber Device to Keep Tip Clean and filed on Oct. 21, 2021. The subject matter of each of the above-mentioned applications is hereby incorporated by reference herein in its entirety.

FIELD OF THE DISCLOSURE

The present application relates to a surgical device. More particularly, the present application relates to a surgical device having a primary cutting feature and a secondary cutting feature. Still more particularly, the present application relates to a surgical cutting device having a regular cutting device and a precision cutting device, where the precision cutting device is equipped with a tip cleaning system.

BACKGROUND OF THE DISCLOSURE

The background description provided herein is for the purpose of generally presenting the context of the disclosure. Work of the presently named inventor(s), to the extent it is described in this background section, as well as aspects of the description that may not otherwise qualify as prior art at the time of filing, are neither expressly nor impliedly admitted as prior art against the present disclosure.

Suture ligation with subsequent cutting of blood vessels to maintain hemostasis during surgery is time-consuming and skill intensive. Energy-based electrosurgical and ultrasonic devices are often used to replace sutures and mechanical clips to provide rapid hemostasis and decrease surgery time. Some of these devices may create undesirably large collateral zones of thermal damage and tissue necrosis or require separate mechanical blades for cutting.

One particular example of this difficulty relates to endometriosis procedures. During this procedure, large legions may be removed from and around the uterus and ovaries. While large legions may be removed using energy-based electrosurgical tools such as a bipolar forceps with an internal cutting blade, many more intricate adhesions may exist in, on, and/or around the nerves, ureter, bowel, ovaries, etc. Using such a tool to address these more intricate adhesions on delicate functioning organs, vessels, and other bodily features may have a high risk of damaging them.

SUMMARY

The following presents a simplified summary of one or more examples of the present disclosure in order to provide a basic understanding of such examples. This summary is not an extensive overview of all contemplated examples and is intended to neither identify key or critical elements of all examples, nor delineate the scope of any or all examples.

In one or more examples, a surgical device may include a housing configured for handling by a user and comprising a plurality of operator interfacing features. The device may also include a patient interfacing tip arranged at, or spaced apart from, a distal end of the housing and controllable by the operator interfacing features. The patient interfacing tip may include a pair of jaws configured to grasp tissue, an electrode on each jaw configured to seal tissue, and an articulating blade configured to cut tissue in a grasp of the pair of jaws. The device may also include an optical element extending from the housing to the patient interfacing tip and configured to emit laser energy to cut tissue. The pair of jaws, the electrode, and the articulating blade may be adapted for coarse cutting of tissue and the optical element may be configured for precise cutting of tissue.

In one or more other examples, a surgical device may include a housing, a patient interfacing tip arrange at or spaced apart from a distal end of the housing and comprising a working channel extending generally longitudinally therethrough. The device may also include an optical element arranged in the working channel and a passive service element. The passive service element may be arranged relative to the working channel and configured for cleaning a distal end of the optical element as the optical element is articulated longitudinally or rotationally.

In one or more other examples, a method of performing a surgical operation may include using a surgical device to perform coarse cutting operations. The coarse cutting operations may include grasping tissue with a forceps, activating a bipolar RF sealing electrode to create a sealed area on the tissue, and advancing a mechanical blade through the sealed area of the tissue. The method may also include using the surgical device to performing precision cutting operations. The precision cutting operations may include positioning an optical element near tissue to be cut and activating a source of laser energy to cut the tissue.

While multiple examples are disclosed, still other examples of the present disclosure will become apparent to those skilled in the art from the following detailed description, which shows and describes illustrative examples of the invention or inventions. As will be realized, the various examples of the present disclosure are capable of modifications in various obvious aspects, all without departing from the spirit and scope of the present disclosure. Accordingly, the drawings and detailed description are to be regarded as illustrative in nature and not restrictive.

BRIEF DESCRIPTION OF THE DRAWINGS

While the specification concludes with claims particularly pointing out and distinctly claiming the subject matter that is regarded as forming the various examples of the present disclosure, it is believed that the subject matter will be better understood from the following description taken in conjunction with the accompanying Figures, in which:

FIG. 18 is a diagram depicting method of use, according to one or more examples.

Corresponding reference characters indicate corresponding parts throughout the several views. Elements in the drawings are not necessarily drawn to scale. The configurations shown in the drawings are merely examples and should not be construed as limiting in any manner.

DETAILED DESCRIPTION

The present application, in one or more examples, relates to a surgical device having a first or primary sealing and cutting system and a second or secondary sealing and cutting system. The primary sealing and cutting system may be well suited for general, coarse, or otherwise relatively imprecise sealing and cutting. This may include sealing and cutting of vessels or tissues spaced apart from sensitive organs, nerves, or other sensitive features of a patient. In one or more examples, the primary sealing and cutting system may include a forceps with a bipolar energy source for grasping and sealing tissue and a blade that is advanceable through the sealed tissue. The secondary sealing and cutting system may be well suited for trimming, for example, or more delicately and precisely cutting vessels or tissues near more sensitive organs, nerves, or other sensitive feature of a patent. In one or more examples, the secondary sealing and cutting system may include a fiber optic laser. As may be appreciated, the distal tip of lasers may have a tendency to experience buildup of a film on the distal tip from smoke or waterborne materials that may be deposited on the distal tip of the laser. Accordingly, the present disclosure also includes a service feature for maintaining a clean distal tip of a fiber optic laser. The service feature may prolong the use of the optical device and/or lengthen the amount of time between removal/cut cycles where a surgeon may remove the laser and clip off the distal tip making the laser suitable for use again.

Figure 1:
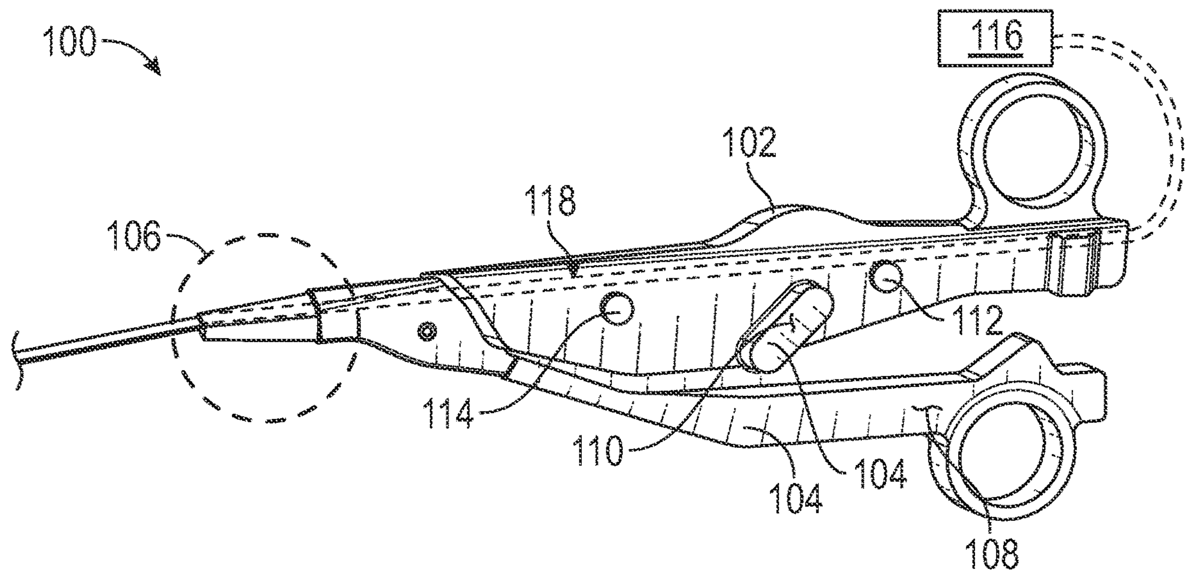
FIG. 1 is a perspective view of a surgical device with dual cutting and service features, according to one or more examples.

FIG. 1 shows a surgical device 100, according to one or more examples. The surgical device 100 may be configured, at least in part, for grasping, sealing, and/or cutting tissue. In one or more examples, the surgical device 100 may include multiple systems for sealing and/or cutting tissue. The surgical device may include a housing 102, one or more actuation or control features or other operator interfacing features 104, and a patient interfacing tip 106.

The housing 102 may be adapted to house, protect, or contain mechanical, electrical, optical, and/or fluid-based components that connect operator interfacing features 104 with corresponding aspects of the patient interfacing tip 106. The housing 102 may include a shell forming the housing 102 and defining and internal cavity, lumen, or other passageway for the components to be arranged in and/or pass through the housing 102. The outer surface of the shell may be configured for handling by the operator and, as such, may include a contoured surface, one or more grips, finger loops, handles, and/or other graspable elements. As shown, the present example, may include thumb loop, for example.

The operator interfacing features 104 may be arranged on and/or around the housing 102 for triggering, actuating, advancing/retracting, and/or otherwise controlling the one or more portions of the patient interfacing tip 106. For example, the operator interfacing features 104 may include jaw actuator 108. The jaw actuator 108 may include a scissor handle as shown or a trigger or other lever or a button or plunger may be provided for opening and closing a pair of jaws on the patient interfacing tip 106. The lever or button/plunger may be operably coupled to one or more push/pull rods, shafts, tubes, pulley systems, or other tension/compression elements arranged within the housing 102 and coupled to one or more jaws at the patient interfacing tip 106. As such, actuation of the lever or button/plunger may cause the jaws to open and close allowing the user to grasp and/or release tissues, vessels, or other aspects of a patient's anatomy.

As another example, the operator interfacing features 104 may include a blade actuator 110. Like the jaw actuator 108, the blade actuator 110 may include a scissor handle, trigger, or other lever or a button or plunger may be provided for advancing and retracting a cutting blade on the patient interfacing tip. In this case, a lever on the side of the housing 102 is shown. The lever or button/plunger may be operably coupled to one or more push/pull rods, shafts, tubes, pulley systems, or other tension/compression elements arranged within the housing 102 and coupled to a cutting blade at the patient interfacing tip 106. As such, actuation of the lever or button/plunger may cause the blade to advance to cut tissues, vessels, or other items and then retract.

Still another example of an operator interfacing feature 104 is a bipolar power actuator 112. Again, the actuator may take one of the several forms mentioned (i.e., scissor handle, trigger, or other lever or a button or plunger). In this case, the actuator may be in electrical communication with jaws or with a separate switch in electrical communication with the jaws such that when the bipolar power actuator 112 is triggered, power may be delivered through the housing to bipolar leads at the patient interfacing tip 106 so as to seal, cauterize, or otherwise treat tissue with electrical energy or heat. A button 112 is shown for this purpose on FIG. 1.

Yet another example of an operator interfacing feature 104 is a laser actuator or actuation system 114. Again, one of the several types of actuators mentioned or another type of actuator may be provided on, near, or around the housing 102 to activate the laser. In this particular case, a button is shown for laser actuation. The laser actuator 114 may be in mechanical, electrical or other type of communication with a laser source 116 and may function to activate a laser source, for example. The laser source 116 may be arranged on or in the housing or off of the housing, as shown, and radiation from the laser source 116 may be carried optically by an optical fiber, cable, strand, or other optical element 118 through the housing 102 to the patient interfacing tip 106 at a distal end where the radiation in the form of an infrared laser, for example, may be emitted to cut, cauterize, or otherwise treat tissues or features of a patient. In one or more examples, the actuator or system 114 may also include control mechanisms for advancing and/or retracting the optical fiber to extend the fiber out of the patient interfacing tip 106, adjust the amount of extension beyond the patient interfacing tip, or withdraw or retract the fiber back toward and/or into the patient interfacing tip 106. Additionally or alternatively, the actuator or system may include control mechanisms for rotating the optical element relative to the housing and the distal tip.

The laser source 116 may be an infrared laser source, for example, and/or the laser source generate other types of laser radiation including light in the visible spectrum, for example. For example, the laser source may include a Holmium-YAG laser or another solid state or other type of laser may be used. In one or more examples, multiple sources 116 and/or corresponding actuators 114 may be provided together with multiple optical elements 118, for example. In one or more examples, the optical element 118 may include single-mode fiber or multi-mode fiber may be provided.

Figure 2:
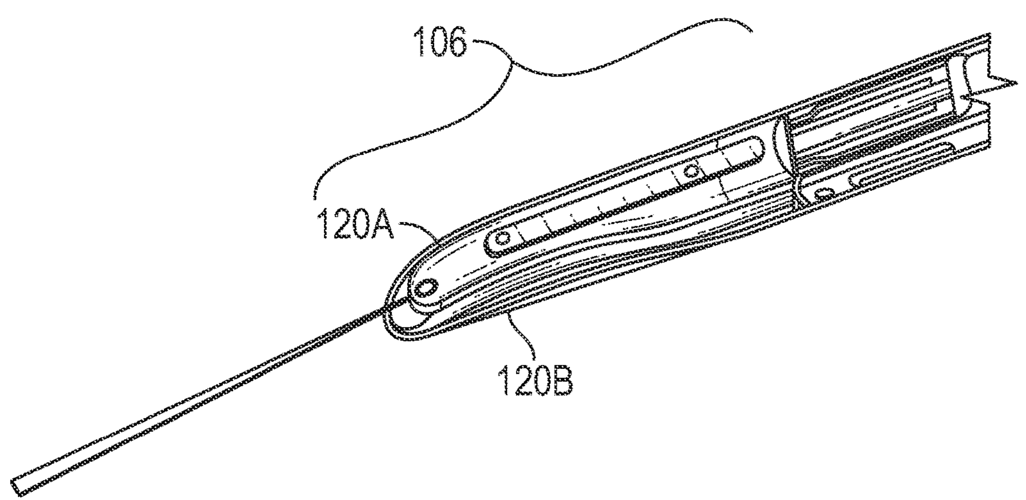
FIG. 2 is a perspective view of a forceps portion thereof, according to one or more examples.
Figure 3:
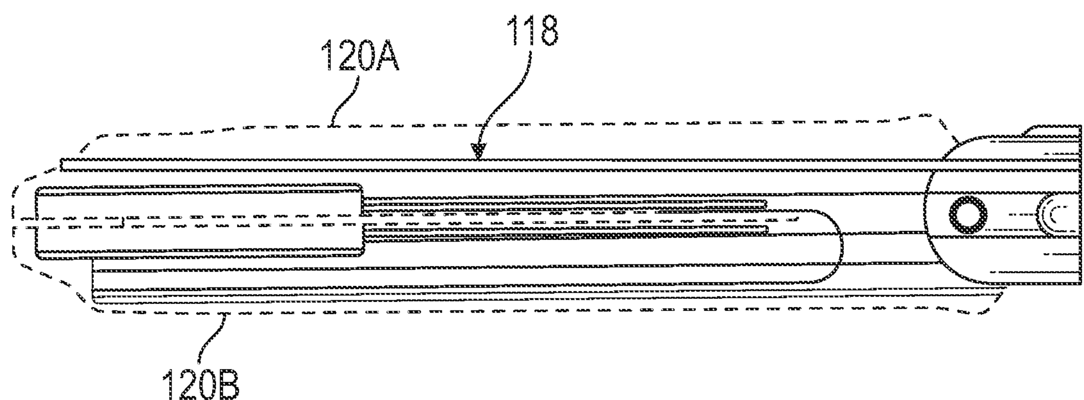
FIG. 3 is a close-up side transparent view thereof.
Figure 4:
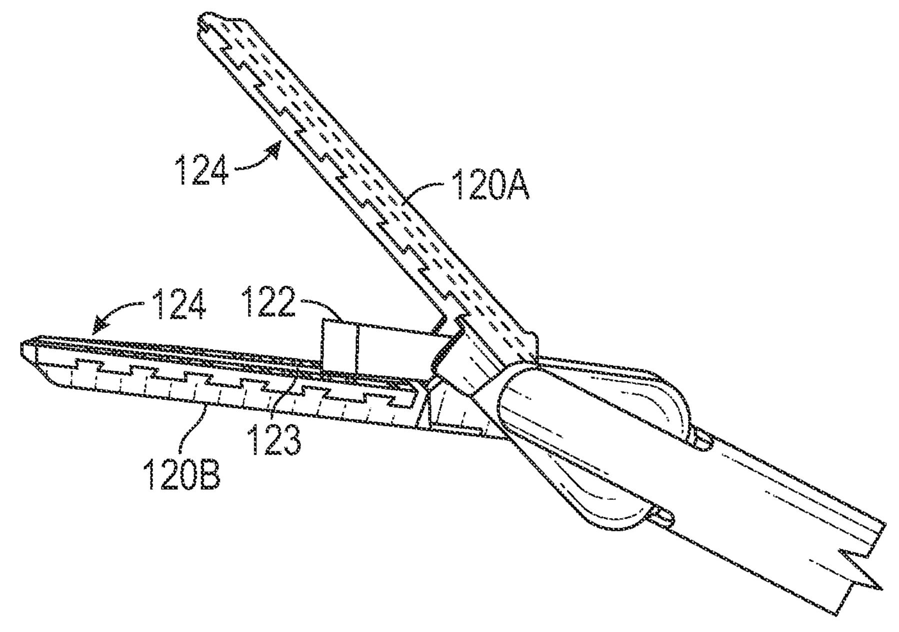
FIG. 4 is a perspective side view thereof with the forceps in an open position.

Turning now to FIGS. 2-4, a patient interfacing tip 106 is shown. The patient interfacing tip 106 may be arranged at or near the distal end of the housing 102 as shown in FIG. 1. However, while the device of FIG. 1 shows the distal interfacing tip 106 immediately adjacent a distal end of the housing 102, extension members and/or systems more suitable for minimally invasive surgery may be provided that offset the patient interfacing tip 106 from the housing 102 and allow for insertion through trocars or other ports provided on a patient for insertion of devices. In either case, the patient interfacing tip 106 may include end effectors or portions thereof referenced above such as a pair of jaws, a cutting blade, bipolar electrodes, a tip of the optical fiber for laser treatment and/or other patient interfacing tools or features.

The jaws 120A/B may be adapted to open and close so as to grasp and release vessels, tissue, or other items within a patient. As shown in FIG. 4, the device may include two articulating jaws 120A/B where both jaws 120A/B are moveable relative to the housing 102 or an extension thereof. In other examples, one of the jaws may be fixed and a single moveable jaw may be provided. In either case, the jaws 120A/B may be operably connected to the jaw actuator 108 via linkages, or other components within the housing 102 and/or extension thereof.

The cutting blade 122 may be adapted to cut vessels or tissues and, in particular, may be adapted to cut vessels or tissues that are within the grasp of the jaws 120A/B. For example, as shown best in FIG. 4, a longitudinally extending slot 123 may be provided on the inner surfaces of the jaws 120A/B. When the jaws 120A/B are closed, the respective slots 123 therein may align with one another and define a passageway for advancing of the blade 122 within the jaws 120A/B. Accordingly, the jaws 120A/B may grasp and hold tissue or vessels and the blade 122 may be advanced within the jaws 120A/B to cut the vessels or tissue. The blade may be operably coupled to the blade actuator 110 at the housing 102 such that when the blade actuator 110 is depressed or otherwise actuated, the blade 122 may advance and when the blade actuator 110 is released, the blade 122 may retract. That is, the blade 122 may be biased in a retracted position, for example. While a mechanical blade 122 has been shown and described, a radio-frequency (RF) cutting device, or an ultrasonic cutting device, or other primary cutting device may be provided.

The bipolar electrodes 124 may be arranged on inner surfaces of the jaws 120A/B so as to pass electrical energy through tissue from one electrode to another when vessels or tissues are grasped by the jaws 120A/B. The electrodes 124 may define a width across the jaws 120A/B that extends beyond the sides of blade slots 123 by a defined margin. As such, when the jaws 120A/B close on tissue and the bipolar electrodes are energized, a seal may be created in the tissue. Moreover, when the blade 122 is advanced through the tissue, the position of the blade 122 relative to the electrodes may help to ensure that a seal is present on each side of the blade 122 and, thus, on each of the separated ends of the cut tissue or vessel. The bipolar electrodes 124 may be in electrical communication with an electrical source such as an RF current generator or other electrical source and the bipolar actuator 112 on the housing 102 may cause the generator to power on or may otherwise selectively place the electrodes 124 on the jaws 120A/B in electrical communication with the generator. While RF energized jaws have been described, still other types of energy may be provided such as ultrasonic energy, resistive heating and other types of energy.

The distal end including a tip of the optical element may be arranged on, in, adjacent to, or around the patient interfacing tip 106. For example, as shown an optical fiber, cable, strand, series of strands or other optical element, may extend from a laser source 116, through the housing 102, and any extension thereof, to the patient interfacing tip 106. At the patient interfacing tip 106, the optical element 118 may pass into and through the patient interfacing tip 106 in a longitudinal fashion to a port or orifice at a distal end of the patient interfacing tip 106. The optical element may, thus, be advanced out of and retracted into the orifice as needed for treatment. That is, for example, the optical element 118 may be advanced out of the distal end of the device to expose the distal end of the optical element 118 and position it a selected distance from vessels, tissues, or other intended treatments sites of the patient. For example, the distal end of the optical element may be positioned such that distal end of the optical element 118 is arranged at or near a distance from the treatment site equal to the focal length of the laser. Other selected distances may also be used. In one or more examples, the optical element or passageway in which it is arranged, may be arranged longitudinally so as to be directed in the same, or generally the same, direction as the patient interfacing tip 106. In other examples, the passageway may be at an angle to the patient interfacing tip 106. In still other examples, an optical manipulator may be present on the patient interfacing tip 106 to control the direction of the optical element 118 as it extends from the patient interfacing tip 106.

While a particular set of features of the patient interfacing tip 106 have been shown and described, still other features, other types of end effectors and/or combinations of end effectors or features thereof may be provided or used. For example, other grasping, sealing, or cutting devices may be provided as well as cautery elements, hemostasis elements, dissection elements, tissue extraction elements, irrigation, suction, or other features. As such, the laser features including the source 116, the optical element 118, and the devices described below with respect to servicing the optical element 118 may be provided on any surgical or electrosurgical device or other device including, but not limited to electrosurgical forceps, vessel sealers, tissue coagulators, tissue cutters, graspers, monopolar pencils, mechanical devices such as mechanical scissors and the like. In still further examples, the laser features may be provided alone and without a primary sealing and cutting system.

Turning now to FIGS. 5-17, a series of service elements are shown. As may be appreciated, optical elements 118 for lasers rely on transmission of radiation from an emitting tip and may suffer degradation during use due to deposits that may build up on the tip. That is, smoke (where cautery, dissection, or other tissue treatment is performed in air) or waterborne matter (where tissue treatment is performed in fluid) may build up and/or be baked onto the tip. As the deposits increase, the effectiveness/efficiency of a laser may continue to degrade. In some situations, when deposits get sufficiently heavy, surgeons may pull optical elements of lasers out of the device, cut off the tip, and reinsert the optical element such that further laser procedures may be performed. The service element of the present disclosure may assist with ongoing and/or in situ service of the tip of the optical element 118 to maintain the efficiency of a laser, for example.

One example of a service element 126 is shown in FIGS. 5-11. As shown, the service element 126 may be a passive service element configured to scrub, wipe, or otherwise clean the tip of the optical element 118 as the optical element 118 is advanced relative to the surgical device 100. As such, a user may retract and advance the device, from time to time, to clean or clear the tip allowing for ongoing servicing and use without fully removing and treating the tip of the optical element 118. The service element 126 may also be adapted for insertion into a bore, lumen, or other port in a distal end of the patient interfacing tip 106 of the surgical device 100. As shown, the service element 126 may include plug, anchor or other securing component 128, a centering component 130, and a series of cleaning elements 132 arranged therein.

The securing component is shown in FIGS. 5-9. As shown, the securing component may be adapted for removable securitization of the service element into a bore, lumen, working channel 134, or other port in the surgical device 100. To this end, the securing component 128 may include an insertion portion 136 and a flange 138. The insertion portion 136 may include a tubular element adapted and sized for insertion into a working channel 134 of the surgical device 100. The tubular element may have a generally annular cross-section, though other cross-sectional shapes may be provided and coordinated with the cross-sectional shape of the working channel. In one or more examples, the tubular element may include ribs 140 extending longitudinally along an outside surface thereof that are relatively thin so as to be crushable when the tubular element is inserted into the working channel 140 of the surgical device 100. That is, the tubular element may be tapered or cylindrical and sized such that when the tubular element is inserted into the working channel 140, the outside surface of the tubular element is substantially similar in diameter to the working channel 140 and the ribs on the outside surface may crush upon insertion to provide a friction fit of the tubular element into the working channel 140. Alternatively or additionally, the tubular element may threadably engage the working channel 140 or retainer clips may be provided or still other engagement features providing for removable engagement of the securing component may be provided. Moreover, while the service element 126 has been shown to fit within the working channel and/or recess into the tip of the device, the service element 126 may alternatively or additionally be externally mounted and extend away from the surface of the device. In these examples, the service element 126 may thread over a stem, clip to nubs on the exterior surface of the device or otherwise fasten to the device and align with the working channel.

Figure 5:
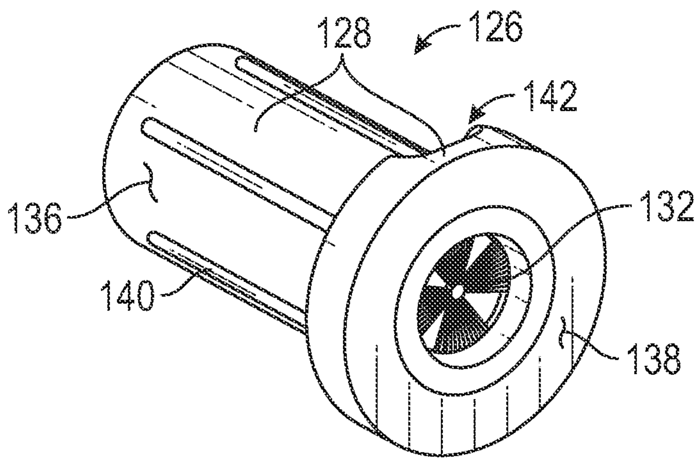
FIG. 5 is a perspective view of a service feature for a distal end of an optic fiber of the surgical device of FIGS. 1-4, according to one or more examples.

The flange 138 may have an annular shape with an inner bore diameter that is the same or similar to an inner bore diameter of the tubular element and an outer diameter that is larger than an outer diameter of the tubular element. As such, when the securing component 128 is inserted into the working channel 140 of the surgical device, the flange 138 may function to stop inward motion of the securing component 128 and hold the distal end of the securing component 128 at or near the distal surface of the working channel 140. As shown in FIG. 5, a pry out groove, recess, or other access feature 142 may be provided on a proximal surface of the flange 138 to allow for prying out of the securing component 128 when replacement, maintenance, or other treatment of the servicing element 126 is desired. A method 600 of reprocessing a device is described in further detail in FIG. 19.

Figure 6:
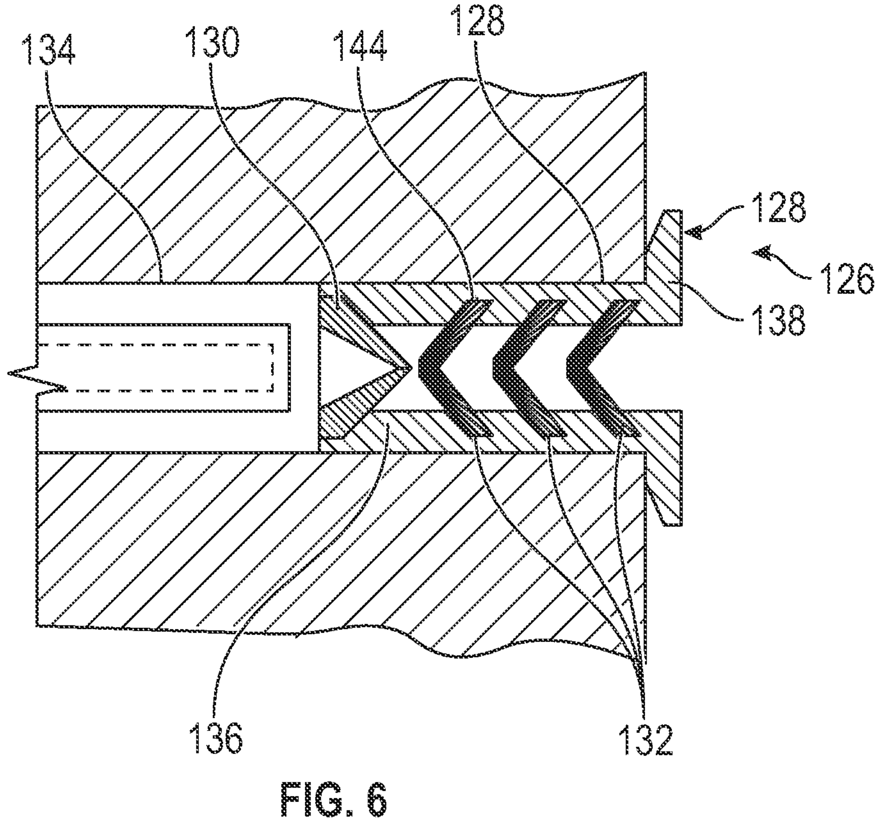
FIG. 6 is a cross-sectional view thereof with the optic fiber in a retracted position, according to one or more examples.

Turning now to FIG. 6, the centering component 130 is shown. The centering component 130 may be configured to control the position of the optical element 118 as it advances and retracts within the working channel 140 at the distal end of the surgical device 100. By controlling the position of the optical element 118, the centering component 130 may assist to hold the tip of the optical element 118 in optimal or at least suitable position for cleaning by the cleaning elements 132. In one or more examples, the centering component 130 may include a conical element pointed distally such that an advancing tip of an optical element 118 is guided toward a center of the working channel as it passes into and through the centering component 130. The conical shape may be advantageous due to its flexibility to accommodate various diameters of optical elements 118. The centering component 130 may be a flexible and/or resilient material such as a polymeric material, elastomer polymer, rubber, silicone, or other suitable material, for example. The centering component 130 may be arranged at a proximal end of the tubular element such that centering can occur as the optical element 118 approaches the service element 126 and the cleaning elements 126 arranged therein. The centering component 130 may include an orifice at the tip of its conical shape that is adapted to allow passage of the optical element 118. The orifice size may be selected to be slightly smaller than a diameter of the optical element 118 such that some stretching occurs when the optical element 118 is advanced through the centering component 130. The centering component 130 may be relatively thin and, in combination with being resilient, may stretch to accommodate the diameter of the optical element 118 as it is advanced therethrough. Alternatively, the orifice may be sized to allow generally free motion of the optical element through the centering component once the optical element is centered.

Figure 10:
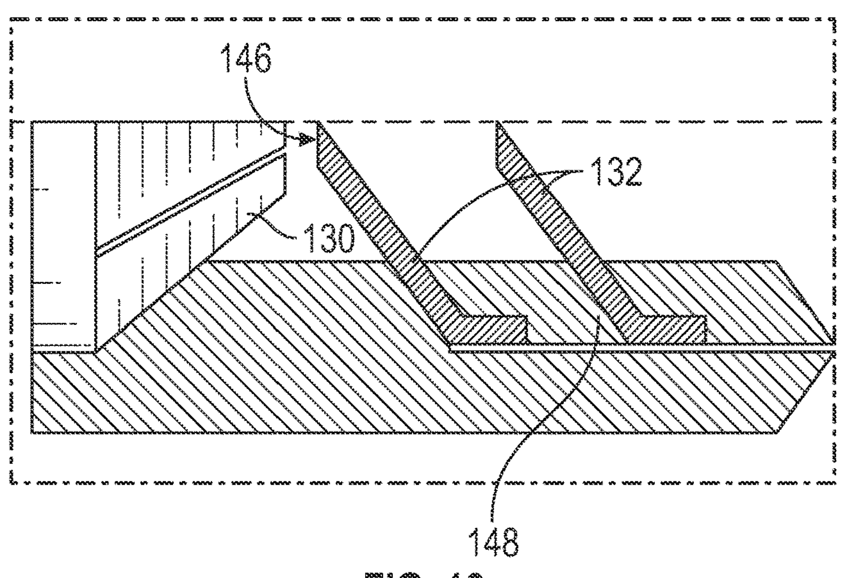
FIG. 10 is a close-up internal view of cleaning elements within the service feature, according to one or more examples.
Figure 11:
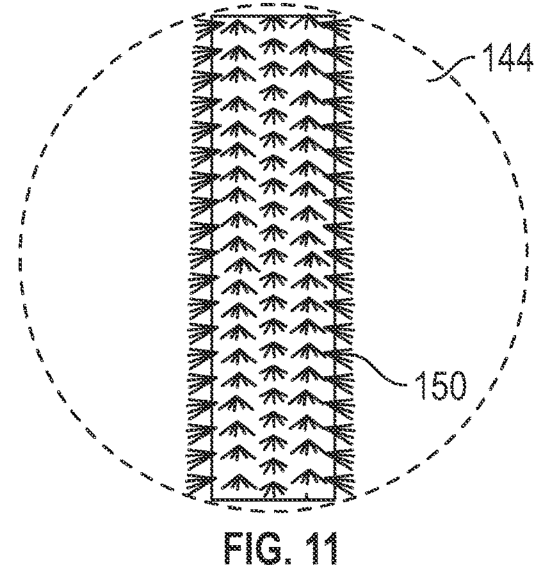
FIG. 11 is a detail view of the cleaning elements.

With continued reference to FIG. 6, a series of cleaning elements 132 may be provided on an interior surface of the securing component 128. A cleaning element 132 may include a scrubber, wiper, or other surface contacting element 144 or non-contact cleaning elements (fluid jets) may be provided. In FIG. 6, the cleaning element 132 includes a scrubber in the form of bristles adapted to engage the tip of the optical element 118 as it is advanced through the inner bore of the securing component 128. As shown, the bristles may be provided in groups to form a cleaning element 132. In one or more examples, the groups may include a plurality of bristles 144 arranged along an inner circumference of the securing component 128. The bristles 144 may be directed annularly inward and tipped in a proximal direction to form a conical arrangement of bristles 144 where the resulting cone is pointed in a proximal direction. Alternatively, the bristles 144 may be tipped in a distal direction or they may extend radially inward. As shown in FIG. 10, the group of bristles 144 may be selected, arranged, and/or trimmed to establish a proximally facing flat and/or annularly shaped contact surface 146 for engaging the tip of the optical element 118. Each cleaning element 132 (e.g., group of bristles) may be retained in the securing component 128 with a retainer 148 as shown. While the bristle tips may be adapted to clean the tip, additional micro-bristles 150 may be arranged along the length of the bristles to provide an additional cleaning effect as shown in FIG. 11. As shown, multiple cleaning elements 132 may be provided such as two, three, or more cleaning elements 132. In one or more examples, each cleaning element 132 may be slightly differently adapted. For example, one set may be adapted for chipping and may have bristles 144 with a relatively high stiffness, while one set may be adapted for scrubbing and may have bristles 144 with a relatively average stiffness, and another set may be for wiping and may have bristles 144 with a relatively low stiffness and/or soft bristles may be provided. In one or more examples, more aggressive cleaning elements 132 may be tipped in a proximal direction and less aggressive cleaning elements 132 may be tipped in a distal direction. For example, the above combinations of cleaning elements 132 may have chipping and/or scrubbing cleaning elements 132 tipped in a proximal direction and wiping elements 132 tipped in a distal direction, for example. The bristles 144 may include one or more types of suitable elements depending on the desired cleaning effect such as extensions, fingers, nubs, bumps, gauze-like material, fabric, cellulose, mesh, metal, and the like.

Figure 7:
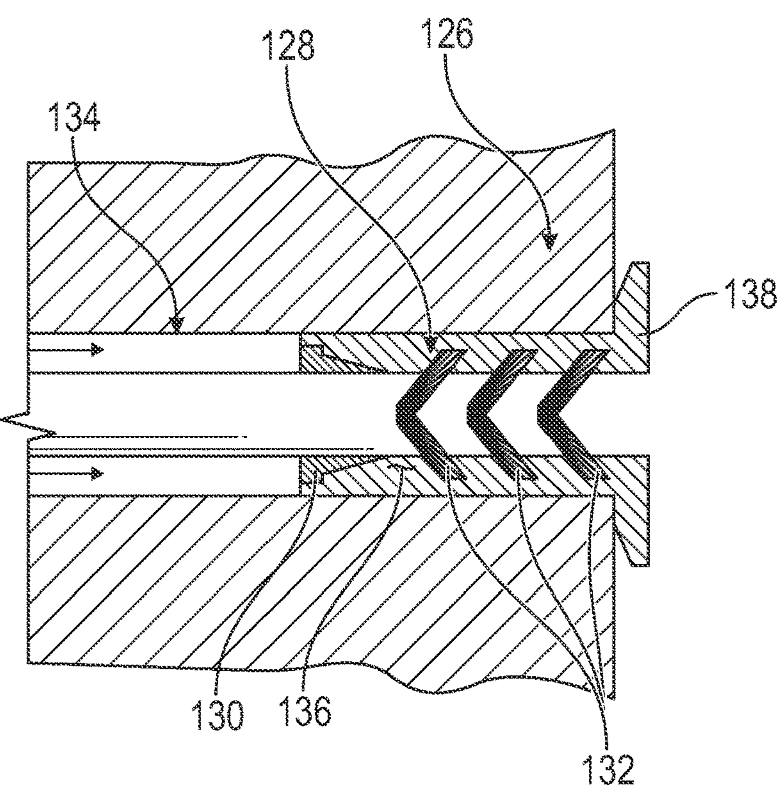
FIG. 7 is an additional cross-sectional view thereof with the optic fiber in a more advanced position, according to one or more examples.
Figure 8:
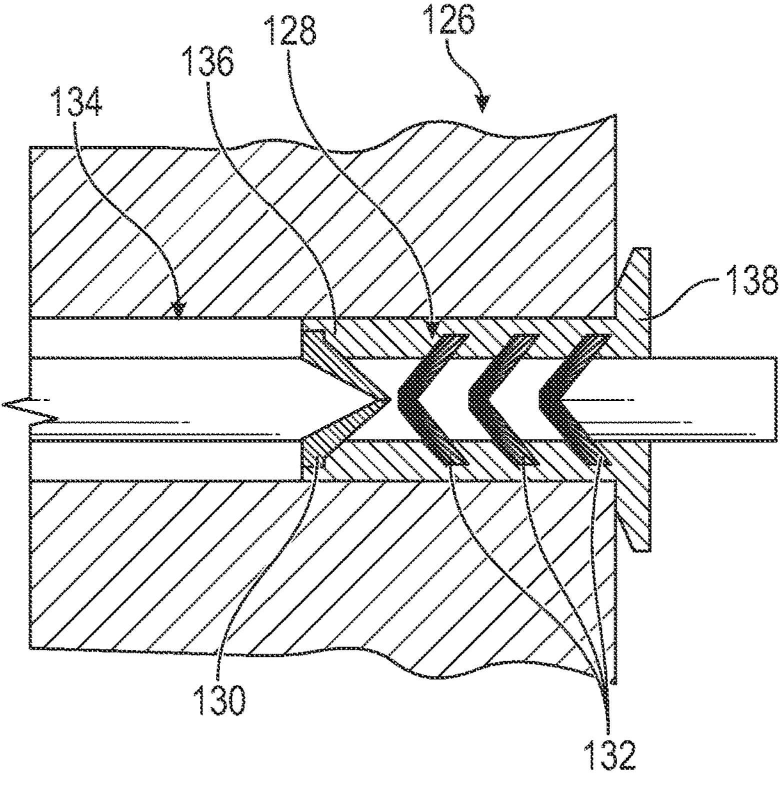
FIG. 8 is an additional cross-sectional view thereof with the optic fiber in a deployed position, according to one or more examples.
Figure 9:
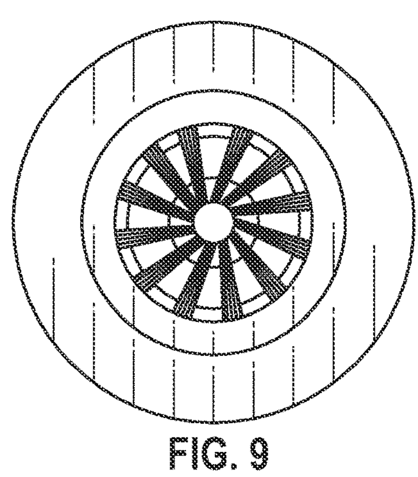
FIG. 9 is a distal end view of the service feature, according to one or more examples.

As depicted in FIGS. 6-8, as an optical element 118 becomes obscured during use, a user may retract and advance the tip of the optical element 118 into and out of the service component 126 in a reciprocating fashion so as to clean or scrub the distal tip of the optical element 118. FIG. 6 shows the distal tip approaching the service element 126. FIG. 7 shows the distal tip having passed through the centering component 130 and engaging a first and second cleaning element 132. FIG. 8 shows the distal tip extending beyond the working channel 140 and the service element 126 arranged thereon and poised to deliver laser treatment.

It is to be appreciated that while the centering component 130 and the cleaning elements 132 have been described as being arranged within a securing component 128, these elements may, alternatively or additionally, be arranged within the bore, lumen, port, or working channel 140 of the device without a securing component 128. That is, the plug, anchor, or other securing component 128 makes them removable and replaceable (e.g., disposable) and other approaches may involve more permanent placement of these elements within a working channel 140 of a surgical device. Moreover, while replaceability may often be considered to involve varying degrees of invasiveness (e.g., anything may be considered replaceable to some degree), the present application considers replaceability to involve removing by hand and/or with minimal tools such as a prying device, a wrench, a plier, or other similar and basic hand tools. Moreover, the arrangement of the securing component 128 at a distal end of the working channel 140 with an exposed flange on the surface reflects that replaceable also does not involve opening up or accessing internal hard to access locations to replace the service element 126.

Figure 12:
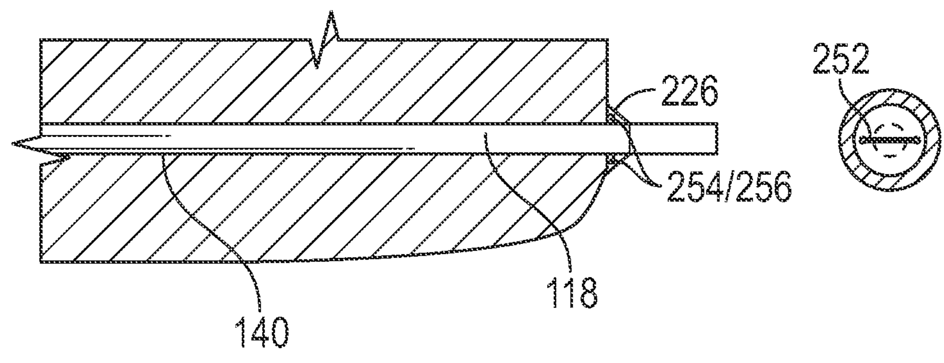
FIG. 12 is a cross-sectional view of another example of a service feature for a distal end of an optic fiber of the surgical device of FIGS. 1-4, according to one or more examples.

FIG. 12 shows another example of a service element 226. As shown, the service element 226 may be a passive service element configured to wipe, scrub, or otherwise clean the tip of the optical element as the optical element 118 is advanced out of the working channel 140 of the device 100. In the present example, the service element 226 may include a membrane arranged over a distal orifice of a working channel 140 of the surgical device 100. The membrane may include a slit or a series of slits 252 that allow passage of the optical element 118 through the membrane. That is, the membrane may include a resilient material such as a polymeric material, elastomer polymer, rubber, silicone, or other suitable material that may stretch to allow passage of the optical element 118 through the membrane. In one or more examples, the membrane may include an internal cleaning feature 254 such as an abrasive surface, bristles, nubs, bumps, or other inward or proximal facing elements adapted to clean the tip of the optical element 118. For example, the user may advance the optical element 118 to an inside surface of the membrane and rotate the optical element 118 to wipe, scrub, or otherwise clean the tip of the optical element 118. Alternatively or additionally, passing the optical element 118 longitudinally through the membrane may function to clean the tip. Moreover, while an internal cleaning feature 254 has been described, the membrane may be provided without the internal cleaning feature 254 and passage through the resilient membrane alone may clean the tip. The membrane may also include a reinforcing rib 256 along the periphery of the slit or slits so as to require some force to be applied to advance the optical element through the membrane and cause the membrane to more forcefully wipe or scrub the tip. Alternatively or additionally, the ends of the slit or slits 252 may include cut-outs or circular shapes so as to resist, arrest, and/or prevent extension of the slits 252 by tearing.

Figure 13:
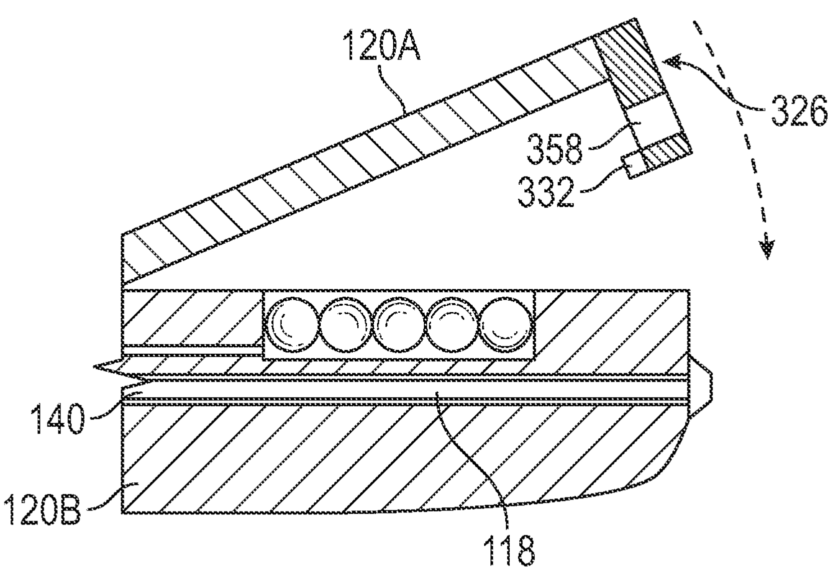
FIG. 13 is a cross-sectional view of yet another example of a service feature for a distal end of an optic fiber of the surgical device of FIGS. 1-4, according to one or more examples.
Figure 14:
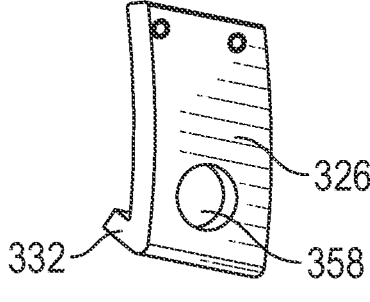
FIG. 14 is a perspective view of a cleaning element of the example of FIG. 13, according to one or more examples.

FIGS. 13 and 14 show another example of a service element 326. As shown, the service element 326 may be an active service element configured to wipe, scrub, or otherwise clean the tip of an optical element 118. The service element 326 in this example may leverage the articulating motion of jaws 120A/B to actively clean a tip of an optical element 118. For example, a tab, flap, or other lateral extending element may be arranged on a distal end of a first jaw 120A and the optical element 118 may be arranged in a second jaw 120B. The tab, flap, or other lateral extending element may be arranged to pass across and wipe, scrub, or clean the tip when the first jaw 120A opens and closes relative to the second jaw 120B. That is, the optical element 118 may be advanced through the second jaw 120B such that a tip of the optical element 118 is arranged at or near the distal end of the second jaw 120B (e.g., at or slightly extending from a working channel 140 thereof). As the first jaw 120A opens and closes, the tab, flap, or other lateral extending element may pass across the tip to clean the tip. In one or more examples, the tab, flap, or other lateral extending element may include an opening or orifice 358. That is, as shown, an opening orifice 358 in the tab/flap may be arranged to align with the working channel 140 or fixed optical element 118 such that when the jaws 120A/B are closed and the tab/flap extends across the end of the optical element, light or other radiation is allowed through the tab/flap so as to allow emission of laser energy, for example.

FIG. 14 shows a tab, flap, or other lateral extending element in isolation from the surgical device 100. As shown, the tab/flap may be secured to the surgical device 100 at an anchor point that may generally hold the tab/flap in a relatively rigid laterally extending position such that deflection of the tab/flap requires that some force along the longitudinal direction of the surgical device be applied. As shown, the tab, flap, or other lateral extending element may include a nub, bump, brush, bristle, or other cleaning element 332 on an inward facing surface that is adapted to contact the tip of the optical element 118 as the tab, flap, or other lateral extending element is moved across the tip. The orifice 358 mentioned above is also shown in the FIG.

Figure 15:
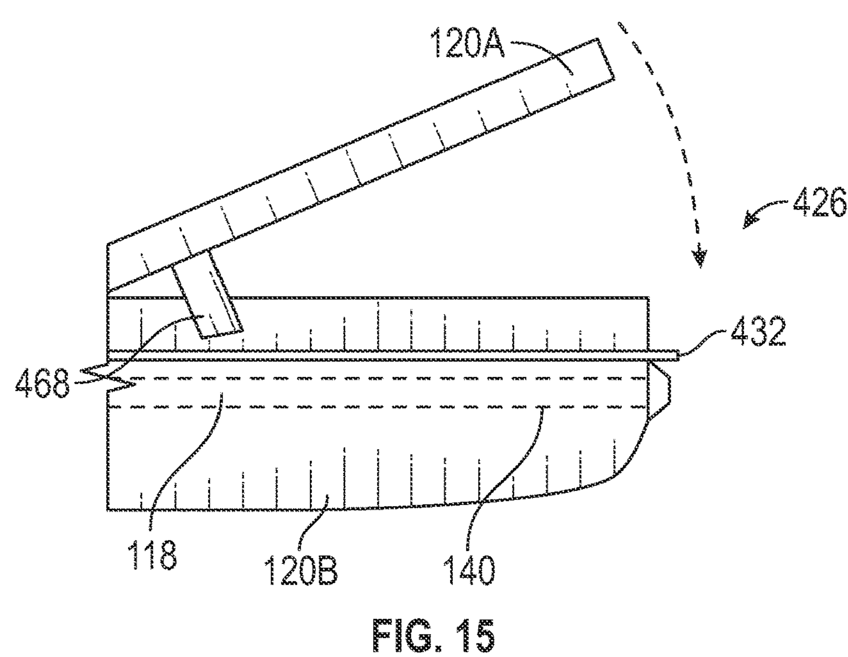
FIG. 15 is a side view of yet another example of a service feature for a distal end of an optic fiber of the surgical device of FIGS. 1-4, according to one or more examples.
Figure 16:
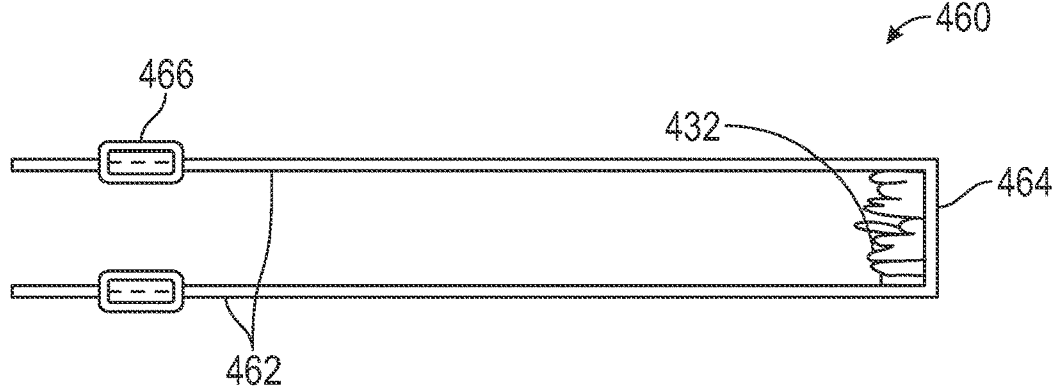
FIG. 16 is a top down view of the service feature in isolation from the surgical device, according to one or more examples.
Figure 17:
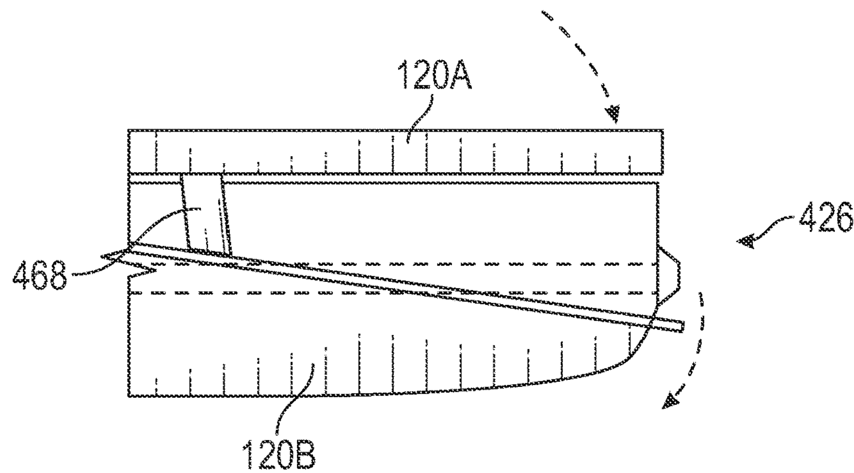
FIG. 17 is another side view of the service feature of FIG. 15 with the service feature having been drawn across the distal tip of the optic fiber, according to one or more examples.

Still another example of a service element 426 is shown in FIGS. 15-17. As shown, the service element 426 may be an active service element configured to wipe, scrub, or otherwise clean the tip of an optical element. Like the example of FIGS. 13-14, the service element 426 in this example may leverage the articulating motion of jaws 120A/B to actively clean a tip of an optical element 118. Here, and as shown in FIG. 16, the service element 426 may include a frame or other structure 460 for supporting a cleaning element 432 across the distal end of the device 100 and lateral to the tip or opening of a working channel 140 extending through the device 100. For example, the frame or other structure 460 may include longitudinally extending rods 462 on either side of the device 100 and a crossing member 464 arranged just passed the distal end of the device and/or just distal to the orifice or opening of the working channel 140 of the device. The frame or other structure 460 or portion thereof may be moveable in conjunction with or based on movement of one of the jaws 120A/B on the device. As shown, for example, the frame or other structure may include a hinge point 466 or contact point (see FIG. 16), and the portion of the frame or other structure distal to the hinge point may be moveable relative to the other portions of the frame 460. Alternatively, a hinge may not be provided and, instead, the structure or frame may be flexible to bend when needed. In one example, the jaws 120A/B of the device may include struts 468 or other contacting elements that cause the moveable portion of the frame to pivot when the jaws 120A/B are opened and closed or that cause deflection of a bendable frame. The pivoting motion of the moving portion or deflecting portion of the frame due to the jaw motion may cause the cleaning element 432 on the frame 460 to move across the tip of the optical element 118 and clean the tip. As with the other cleaning elements, the present example may include a brush, bristle, bump, nub, or other cleaning element adapted to contact the tip and clean the tip or a non-contact cleaning element may be provided. In one or more examples, the hinge point of the frame may be biased to hold the moving portion of the frame in a longitudinal position such that when the jaws are opened, the moving portion will return to a longitudinal position poised to move across the tip when the jaws close. Where the hinge is not provided, the general stiffness of the frame may be selected to bias the frame to a neutral position.

It is to be appreciated that some of the service elements 126/226 described herein have been described as passive or stationary and some 326/426 as active or moving. In the present application, passive service elements 126/226 may be generally stationary and movement of the optical element 118 either through longitudinal articulation, rotation, or other movement of the optical element 118 relative to the service element 126/226 may function to clean the optical element 118. In contrast, active service elements 326/426 may have a moving component such that the optical element 118 may remain generally stationary and the service element 326/426 may move relative to the device 100 and the optical element 118 to clean the optical element.

It is further to be appreciated that the use of a primary and secondary cutting device may be advantageous by providing flexibility of cutting precision. For example, the presently described surgical device 100 may be well suited for various procedures and, in particular, procedures where varying degrees of cutting precision are helpful. For example, in the case of endometriosis, cutting and removal of lesions and other growths around the uterus, ovaries, bowel, bladder, and other functioning portions of the patient may be involved. Where such cutting is spaced a reasonable distance from such functioning portions of the patient, an RF powered forceps and corresponding mechanical cutting blade as described above may be very suitable to seal and cut vessels and tissue. However, such lesions and growths may also be more closely adhered to the these relatively sensitive portions of the patient anatomy and the heat from the RF powered forceps as well as the relatively wide seal area formed when using the RF powered forceps may not be suitable for dissection, resection, or other cutting near and/or on the sensitive portions of the patient. In these cases, the secondary sealing and cutting device in the form of a laser may be used to more intricately seal and cut in, on, or around these more delicate portions of the patient anatomy. Moreover, as this process is performed, a service element may be used to maintain the efficiency of the laser by cleaning the distal tip of the optical element from time to time throughout the procedure without having to remove the optical element and cut off the tip of the optical element.

The presently described devices may also be advantageous due to the removability of the service element, which may allow for removal and replacement of an element that may wear out or is difficult to clean. For example, the bristles or other cleaning features may break, become overly flexible, or otherwise deteriorate making them less effective at cleaning the tip of the optical element. Moreover, in some cases, the bristles may collect tissue, debris, or other material cleaned from the tip of the optical element. The ability to readily remove the service element may provide for a longer life of the underlying surgical device, less costly repair, and/or easier reprocessing. Still further, the passive nature of some of the service elements may cause them to be less likely to break or otherwise fail and may also be effective when used with moveable optical elements. Still other advantages may be associated with the passive nature of the service element.

It is to be appreciated that while an optical element 118 for transmitting laser energy from a laser source 116 to the distal end of the device has been discussed, the optical element 118 may also be a scope, for example, that captures imagery of a procedure by allowing light to pass into a lens on the distal end of the scope. That is, while a tip of an optical element 118 has been referenced above, such tip may alternatively or additionally be a lens of a scope, for example. In this case, the source 116 may be a video processing element with a display and/or recording feature. Still further, while an optical element 118 has been described as, for example, a laser fiber, the distal end of such device may also be a light, for example, for providing a light source to a surgical procedure. In this example, the source 116 may be a power source and the optical element 118 may actually take the form of electrical supply lines supplying power to a light at a distal end. In still another example, the optical element 118 may include multiple optical elements where the optical elements are optical fibers for carrying radiation of differing wavelengths. For example, on optical fiber may carry infrared radiation for tissue cutting or treatment and another optical fiber may carry radiation in the visual spectrum and, as such, may provide for illuminating or pointing to the tissue to be cut by being closely aligned with the infrared radiation directed at the same tissue. Any of the service elements described with respect to FIGS. 5-17 may be used to maintain a clean and/or clear tip, lens, light, or other feature on a distal end of the optical element 118 and may include the passive service elements of FIGS. 5-12 and/or the active service elements of FIGS. 13-17.

It also to appreciated that one or more of the service elements 126/226/326/426 described in FIGS. 5-17 may be used alone or in combination with any of the other service elements 126/226/326/426 shown and described. For example, a passive service element 126/226 may be used in conjunction with an active service element 326/426 or multiple passive service elements 126/226 and multiple active service elements 326/426 may be provided.

Turning now to FIG. 18, a method of use 500 may be provided. As shown, the method 500 may include using a surgical device to perform surgical operations 502 such as, for example, dissection, resection, or other cutting operations using a first or primary sealing and cutting device. The cutting operations may include, for example, grasping tissue or vessels with a forceps 502A and activating a bipolar RF sealing electrode to create a sealed area on the tissue 502B. The cutting operations may also include advancing a mechanical blade through the sealed area to cut the tissue 502C. This process of using a primary sealing and cutting device may be used to perform a series of cutting operations on a patient that allow for coarse cutting techniques and, for example, do not impart excessive heat to surrounding or adjacent patient organs or features such as the uterus, ovaries, bowel, bladder, ureters, or other sensitive aspects of the patient's anatomy. The method may also include performing finer more precise cutting with the same surgical device that is equipped with an integrated laser as described herein 504. This portion of the method may include positioning a distal end of a laser at or near tissue to be cut 504A. This step may include advancing the laser out of the end of the device or (where the laser is fixed in the device) positioning the device such that a suitable distance is provided between the end of the optical element and the target (e.g., a distance equal to the laser focal length, a fraction thereof, or a multiple thereof). The method may also include activating a laser source to generate laser energy that is emitted out of the distal end of the optical element to cut or otherwise treat tissue 504B. The method may also include in situ service or cleaning of the tip on the optical device. For example, the method may include articulating the optical element longitudinally by advancing and retracting the optical and engaging a passive service element with the tip of the optical element and/or rotating the optical element to rotationally engage the tip of the optical element with a passive service element. Alternatively, or additionally, the method may include cleaning the tip of the optical element with an active service element. Still other steps may be provided and the steps described herein may be performed in other orders that are suitable based on the procedure being performed.

Figure 19:
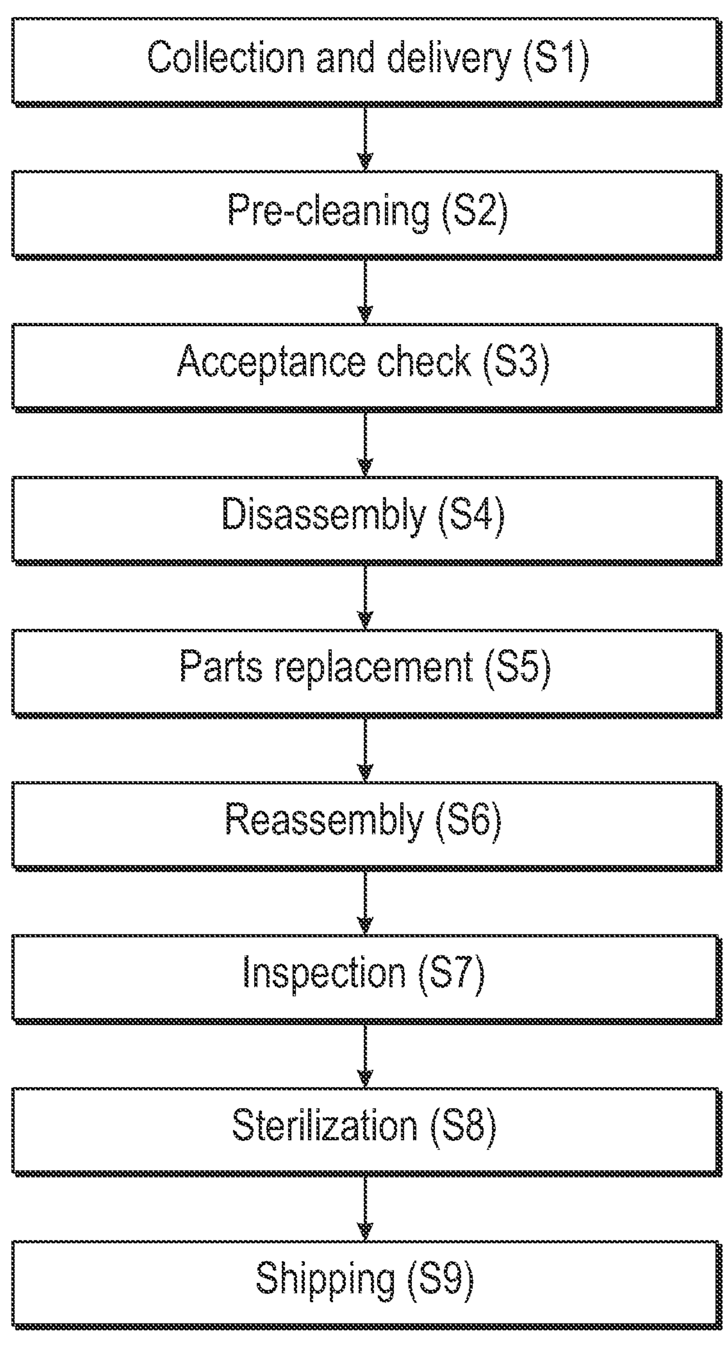
FIG. 19 is a diagram depicting a method of reprocessing, according to one or more examples.

As mentioned, the device described or one or more parts thereof may be configured for reprocessing. FIG. 19 is a flowchart describing the reprocessing method 600 for the device 100. The device 100 described above may be disposed of after one use, or may be repeatedly used a plurality of times. In the case of a configuration that is repeatedly used a plurality of times, for example, reprocessing method shown in FIG. 19 may be used. An operator who remanufactures may collect the used device 100 after it has been used for treatment and may transport it to a factory or the like (Step S1). The used device 100 may be transported in a dedicated container to prevent contamination from the device 100.

Then, the operator cleans and sterilizes the collected and transported used device 100 (Step S2). Specifically, in cleaning the device 100, deposits adhering to the jaws 120A/B, the blade 122, the optical element 118, the service element 126/226/326/426 or other aspects of the device 100 are removed by using a brush or the like. After that, to remove pathogenic microorganisms and the like derived from blood, body fluid, etc., the device 100 is used with any cleaning solution of isopropanol-containing cleaning agent, proteolytic enzyme detergent, and alcohol. And one or more of the above-referenced aspects of the device 100 are cleaned. The cleaning liquid is not limited to the cleaning liquid described above, and other cleaning liquids may be used. Further, in the sterilization of the device 100, to sterilize the pathogenic microorganisms and the like adhering to the mentioned aspects of the device 100, any of high-pressure steam sterilization, ethylene oxide gas sterilization, gamma ray sterilization, hydrogen peroxide and hydrogen peroxide low temperature sterilization is used. The mentioned aspects of the device 100 have accessible surfaces and are, therefore, easy to clean. In some examples, the working channel 134 of the device 100 may be cleaned or subsequently cleaned again after removing the service element 126/226/326/426 and/or the optical element 118 from the working channel. This allows the distal portion of the surface of the working channel 134 obscured by the service element to be cleaned.

The operator may perform an acceptance check of the used device 100 (Step S3). In detail, the operator checks whether the used device 100 has significant defects or the used device 100 exceed a maximum number of reprocessing.

Next, the operator may disassemble the used device 100 (Step S4). Specifically, the operator may remove the service element 126/226/326/426 from the device 100. As discussed, for example, part 126 can connect to the device 100 by a friction fit in the working channel 100 and is, thus, removeable from device 100, such as by prying it out. In some examples, disassembly may include unscrewing threads instead of prying out a friction fit, or any other suitable fastening feature.

After the step S4, some parts may be replaced (Step S5). For example, the service element 126/226/326/426 may include difficult to clean bristles or other cleaning elements and, as such, may be replaced during the reprocessing process. Therefore, there is advantage that it is easy to replace the service element in the Step S5.

After step S5, the operator assembles a new device 100 (Step S6). In detail, the new device 100 is assembled by replacing the service element 126, for example. Therefore, there is advantage that it is easy to assemble in the Step S6.

In some examples, Step S6 can include adding an identifier to indicate the device has been modified from its original condition, such as adding a label or other marking to designate the device as reprocessed, refurbished or remanufactured.

After step S6, the operator inspects and tests the newly formed device 100 (step S7). Specifically, the operator who remanufactures verifies that the newly formed device 100 has the same effectiveness and safety as the original product by various functional tests. There is advantage that it is easy to verify in the Step S7.

After Step S7, the operator sequentially performs a sterilization and storage (Step S8), and shipping (Step S9) of the new device 100. In the Step S8, in step S7, a sterilization treatment using a sterilizing gas such as ethylene oxide gas or propylene oxide gas is applied to the new device 100 and the device is stored in a storage container until use.

Steps S1 to S9 described above are executed to achieve reprocessing of the device 100. It is to be appreciated that, while particular order terms are used above, one or more of the steps in the method may be performed out of order depending on the circumstances and if a particular order is not claimed, the specification should not be relied on to require a particular order when assessing the meaning or scope of the claim.

As used herein, the terms "substantially" or "generally" refer to the complete or nearly complete extent or degree of an action, characteristic, property, state, structure, item, or result. For example, an object that is "substantially" or "generally" enclosed would mean that the object is either completely enclosed or nearly completely enclosed. The exact allowable degree of deviation from absolute completeness may in some cases depend on the specific context. However, generally speaking, the nearness of completion will be so as to have generally the same overall result as if absolute and total completion were obtained. The use of "substantially" or "generally" is equally applicable when used in a negative connotation to refer to the complete or near complete lack of an action, characteristic, property, state, structure, item, or result. For example, an element, combination, embodiment, or composition that is "substantially free of" or "generally free of" an element may still actually contain such element as long as there is generally no significant effect thereof.

To aid the Patent Office and any readers of any patent issued on this application in interpreting the claims appended hereto, applicants wish to note that they do not intend any of the appended claims or claim elements to invoke 35 U.S.C. § 112(f) unless the words "means for" or "step for" are explicitly used in the particular claim.

Additionally, as used herein, the phrase "at least one of [X] and [Y]," where X and Y are different components that may be included in an embodiment of the present disclosure, means that the embodiment could include component X without component Y, the embodiment could include the component Y without component X, or the embodiment could include both components X and Y. Similarly, when used with respect to three or more components, such as "at least one of [X], [Y], and [Z]," the phrase means that the embodiment could include any one of the three or more components, any combination or sub-combination of any of the components, or all of the components.

In the foregoing description various embodiments of the present disclosure have been presented for the purpose of illustration and description. They are not intended to be exhaustive or to limit the invention to the precise form disclosed. Obvious modifications or variations are possible in light of the above teachings. The various embodiments were chosen and described to provide the best illustration of the principals of the disclosure and their practical application, and to enable one of ordinary skill in the art to utilize the various embodiments with various modifications as are suited to the particular use contemplated. All such modifications and variations are within the scope of the present disclosure as determined by the appended claims when interpreted in accordance with the breadth they are fairly, legally, and equitably entitled.

What is claimed is:

1. A surgical device, comprising:

a housing configured for handling by a user and comprising a plurality of operator interfacing features;

a patient interfacing tip arranged at, or spaced apart from, a distal end of the housing and controllable by the operator interfacing features, the patient interfacing tip comprising a pair of jaws configured to grasp tissue, an electrode on each jaw configured to seal tissue, and an articulating blade configured to cut tissue in a grasp of the pair of jaws;

an optical element extending from a laser source connecting end at or near the housing to the patient interfacing tip and configured to emit laser energy to cut tissue, the optical element being arranged in a working channel extending through a jaw of the pair of jaws to an orifice at a distal end of the jaw; and an active service element secured to the patient interfacing tip and being operable through a grasping operation of the pair of jaws to pass laterally across and wipe a distal facing tip of the optical element extending out of the distal end of the jaw, wherein the pair of jaws and the articulating blade are adapted for coarse cutting of tissue and the optical element is configured for precise cutting of tissue.

2. The device of claim 1, wherein the optical element is moveable within the working channel.

3. The device of claim 1, wherein the optical element is fixed in the working channel.

4. The device of claim 1, wherein the active service element comprises a laterally extending element arranged on a first jaw of the pair of jaws and further arranged to pass across a distal end of a second jaw of the pair of jaws, where the working channel and optical element are arranged in the second jaw.

5. The device of claim 1, wherein the active service element comprises a frame with a moveable portion that passes across the end of the optical element when the pair of jaws open and close.

6. A surgical device, comprising:

a housing configured for handling by a user and comprising a plurality of operator interfacing features;

a patient interfacing tip arranged at, or spaced apart from, a distal end of the housing and controllable by the operator interfacing features, the patient interfacing tip comprising a pair of jaws configured to grasp tissue, an electrode on each jaw configured to seal tissue, and an articulating blade configured to cut tissue in a grasp of the pair of jaws;

an optical element extending from a laser source connecting end at or near the housing to the patient interfacing tip and configured to emit laser energy to cut tissue, the optical element being arranged in a working channel extending through a jaw of the pair of jaws to an orifice at a distal end of the jaw; and an active service element secured to the patient interfacing tip and being operable through a grasping operation of the pair of jaws to wipe a distal tip of the optical element extending out of the distal end of the jaw, wherein:

the pair of jaws and the articulating blade are adapted for coarse cutting of tissue and the optical element is configured for precise cutting of tissue; and the active service element comprises a laterally extending element arranged on a first jaw of the pair of jaws and further arranged to pass across a distal end of a second jaw of the pair of jaws, where the working channel and optical element are arranged in the second jaw.

* * * * *